(12) United States Patent
Miyake et al.

(10) Patent No.: US 11,397,164 B2
(45) Date of Patent: Jul. 26, 2022

(54) ION CONCENTRATION MEASUREMENT DEVICE

(71) Applicant: Hitachi High-Tech Corporation, Tokyo (JP)

(72) Inventors: Masafumi Miyake, Tokyo (JP); Tetsuyoshi Ono, Tokyo (JP); Satoshi Ozawa, Tokyo (JP); Ukyo Ikeda, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 284 days.

(21) Appl. No.: 16/649,477

(22) PCT Filed: Feb. 4, 2019

(86) PCT No.: PCT/JP2019/003777
§ 371 (c)(1),
(2) Date: Mar. 20, 2020

(87) PCT Pub. No.: WO2019/171852
PCT Pub. Date: Sep. 12, 2019

(65) Prior Publication Data
US 2020/0300809 A1     Sep. 24, 2020

(30) Foreign Application Priority Data

Mar. 6, 2018    (JP) .............................. JP2018-039344

(51) Int. Cl.
*G01N 27/622*   (2021.01)
*G01N 27/417*   (2006.01)
*G01N 27/70*    (2006.01)

(52) U.S. Cl.
CPC ....... *G01N 27/622* (2013.01); *G01N 27/4175* (2013.01); *G01N 27/70* (2013.01)

(58) Field of Classification Search
CPC ............ G01N 27/622; G01N 27/4175; G01N 27/70; G01N 33/48792; G01N 27/4166
(Continued)

(56) References Cited

U.S. PATENT DOCUMENTS

| | | | | |
|---|---|---|---|---|
| 5,453,171 A | * | 9/1995 | Ma ..................... | G01N 27/3335 435/817 |
| 5,496,521 A | * | 3/1996 | Leiner ................ | G01N 27/4162 436/163 |

(Continued)

FOREIGN PATENT DOCUMENTS

| JP | 2007-93252 A | 4/2007 |
|---|---|---|
| JP | 2011-203252 A | 10/2011 |

(Continued)

OTHER PUBLICATIONS

Translation of WO 2017029893 (Year: 2017).*
Extended European Search Report issued in European Application No. 19764262.2 dated May 3, 2021 (seven (7) pages).

(Continued)

*Primary Examiner* — Christopher P McAndrew
(74) *Attorney, Agent, or Firm* — Crowell & Moring LLP (57) ABSTRACT

The invention aims to suppress an effect of noise and heat generated from a memory on a measurement result in an ion concentration measuring device that uses an ion detection element for outputting a potential corresponding to the concentration of ions. The ion concentration measuring device according to the invention includes a cartridge having an ion detection element and a memory and supplies power to the memory in a time period excluding a time period for which the potential generated by the ion detection element is acquired.

11 Claims, 5 Drawing Sheets

(58) Field of Classification Search
USPC .......................................................... 324/71.1
See application file for complete search history.

(56) References Cited

U.S. PATENT DOCUMENTS

| | | | | |
|---|---|---|---|---|
| 5,602,467 | A | * | 2/1997 | Krauss ............... G01N 27/4148 327/307 |
| 5,725,754 | A | * | 3/1998 | Belford ............... G01N 27/122 205/793 |
| 8,008,087 | B1 | | 8/2011 | Shalyt et al. |
| 2003/0203498 | A1 | | 10/2003 | Neel et al. |
| 2012/0175254 | A1 | | 7/2012 | Kobayashi et al. |
| 2017/0350859 | A1 | * | 12/2017 | Brown ................. C12Q 1/6869 |
| 2018/0059043 | A1 | | 3/2018 | Leone |
| 2018/0238829 | A1 | | 8/2018 | Watanabe et al. |

FOREIGN PATENT DOCUMENTS

| | | |
|---|---|---|
| JP | 2013-512447 A | 4/2013 |
| WO | WO 2011/034170 A1 | 3/2011 |
| WO | WO 2011/067559 A | 6/2011 |
| WO | WO 2017/029893 A1 | 2/2017 |

OTHER PUBLICATIONS

Japanese-language International Preliminary Report on Patentability (PCT/IPEA/409) with Annexes issued in PCT Application No. PCT/JP2019/003777 dated Mar. 17, 2020 (nine (9) pages).
International Search Report (PCT/ISA/210) issued in PCT Application No. PCT/JP2019/003777 dated Apr. 9, 2019 with English translation (four (4) pages).
Japanese-language Written Opinion (PCT/ISA/237) issued in PCT Application No. PCT/JP2019/003777 dated Apr. 9, 2019 (four (4) pages).

* cited by examiner

ION CONCENTRATION MEASUREMENT DEVICE

TECHNICAL FIELD

The present invention relates to an ion concentration measuring device.

BACKGROUND ART

As methods for analyzing the concentration of ions within a solution, there are a coulometric titration method, a flame photometry method, an ion-selective electrode method, and the like. The ion-selective electrode method is widely used for the measurement of the concentration of ions within a biological sample and the like, since the concentration of ions within the sample can be quantitated only by inserting an ion-selective electrode together with a reference electrode in a sample solution. Since an ion concentration measuring device using an ion-selective electrode method has advantages that the ion concentration measuring device quickly performs measurement and is easily downsized and does not require a hazardous substance such as a propane gas and is safe, the ion concentration measuring device is embedded in a clinical inspection analysis device to be used in a hospital, an inspection center, or the like and is used.

For the clinical inspection analysis device, information (individual identification codes, usage periods, and usage statuses, and the like) on the device, conditions of use, and the like are demanded to be stored for the purpose of reducing medical errors and for quick handling upon the occurrence of the errors. To meet the demand, a method for implementing a storage medium storing the information in a cartridge with an ion-selective electrode has been proposed (for example, Patent Literature 1). According to this method, when a device fails, the cartridge removed from the failed device is attached to another device, and the device to which the cartridge has been attached takes over the information stored in the storage medium and can continuously performs measurement.

When the method described in Patent Literature 1 is used, it is necessary that a data storage region that is a semiconductor memory or the like be included in the cartridge with the ion-selective electrode. When data is to be written to the data storage region, noise and heat are generated and may affect the data to be written. As a method for suppressing an effect of the noise generated in the data writing, there is a method in which a time period for measuring the potential of the ion-selective electrode does not overlap a time period for writing data to a memory (Patent Literature 2).

CITATION LIST

Patent Literature

Patent Literature 1: WO2011/034170
Patent Literature 2: WO2017/029893

SUMMARY OF INVENTION

Technical Problem

In the invention described in Patent Literature 2, how to control the semiconductor memory for a time period for which data is not written is not specially mentioned. However, regarding a sensor having a high-resistance portion such as a liquid film type ion-selective electrode, even in a state in which data writing to the memory is stopped, noise generated by turning on a power source of the memory affects a measurement result. In addition, it is known that heat is generated from the memory during the time when power is supplied to the semiconductor memory and this heat affects potential measurement.

The present invention has been devised under the foregoing circumstances and aims to suppress an effect of noise and heat generated from a memory on a measurement result in an ion concentration measuring device that uses an ion detection element for outputting a potential corresponding to the concentration of ions.

Solution to Problem

An ion concentration measuring device according to the invention includes a cartridge having an ion detection element and a memory and supplies power to the memory in a time period excluding a time period for acquiring a potential generated by the ion detection element.

Advantageous Effects of Invention

According to the ion concentration measuring device according to the present invention, it is possible to suppress an effect of noise and heat generated from the memory on a measurement result while using an advantage of a measurement method using an ion-selective electrode. In addition, it is possible to use data stored in the memory by removing the cartridge.

DESCRIPTION OF EMBODIMENTS

First Embodiment

Figure 1:
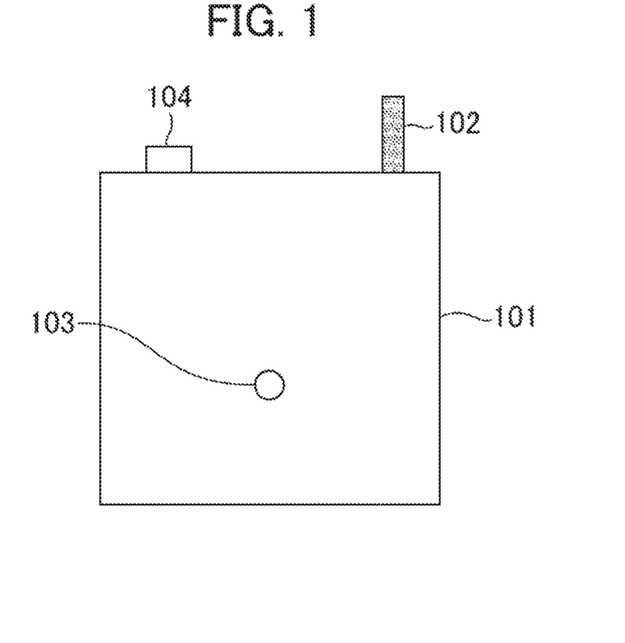
FIG. 1 is an elevation view of a cartridge 101 included in an ion concentration measuring device 100 according to a first embodiment.

FIG. 1 is an elevation view of a cartridge 101 included in an ion concentration measuring device 100 according to a first embodiment. The cartridge 101 includes an internal electrode 102, a flow path 103, and a communication line 104. The internal electrode 102 is an electrode for outputting a potential generated by an ion-sensitive membrane 105 described later. The flow path 103 is a through-hole through which a liquid sample passes. The communication line 104 is connected to a semiconductor memory 106 described later. A reading-writing unit 118 described later accesses the semiconductor memory 106 via the communication line 104 and writes or reads data. The communication line 104 is also used to supply power to the semiconductor memory 106.

Figure 2:
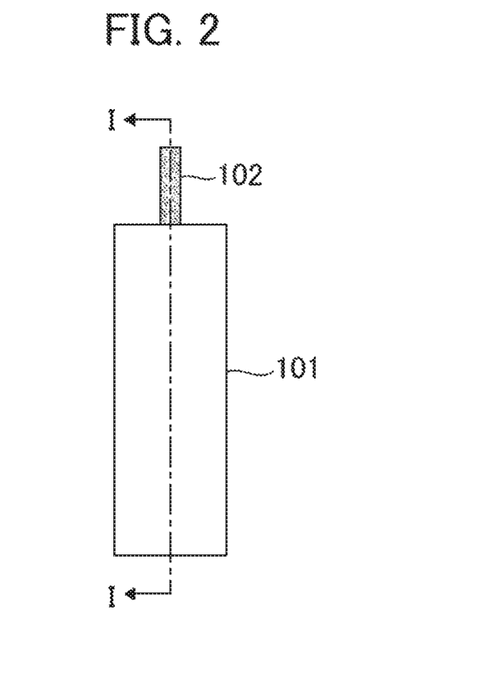
FIG. 2 is a side view of the cartridge 101.

FIG. 2 is a side view of the cartridge 101. A chain line I-I is a section line of FIG. 3 described later. The cartridge 101 can be configured using, for example, resin such as polyvinyl chloride, polystyrene, polypropylene, or the like.

Figure 3:
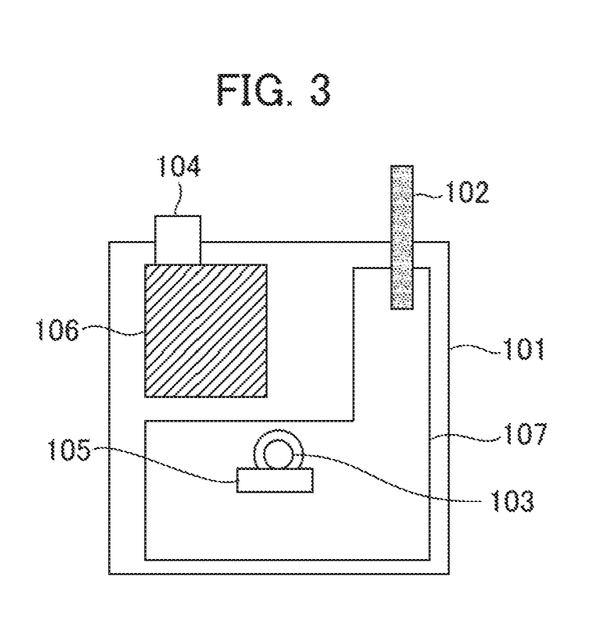
FIG. 3 is a cross-sectional view of the cartridge 101, taken along a chain line I-I of FIG. 2.

FIG. 3 is a cross-sectional view of the cartridge 101, taken along the chain line I-I of FIG. 2. A cutout for enabling the liquid sample to flow out is formed in a portion of the flow path 103. The ion-sensitive membrane 105 is bonded to the flow path 103 to close the cutout. The ion-sensitive membrane 105 is configured so that electromotive force is generated depending on the type and concentration of ions within the sample. The ion-sensitive membrane 105 is constituted by resin such as polyvinyl chloride, polystyrene, polypropylene, or the like, a compound such as a ligand for supplementing ions, or the like. A plasticizer for plasticizing the ion-sensitive membrane 105, a highly fat-soluble ionic compound for removing an effect on ions, or the like may be used.

As the ion-sensitive membrane 105, a membrane of a type corresponding to an ion type to be measured is used. For example, when sodium is measured, a sensitive membrane that responds to a sodium ion is used. When potassium is measured, a sensitive membrane that responds to a potassium ion is used. The ion concentration measuring device for clinical inspection measures a sodium ion, a potassium ion, a chlorine ion, a calcium ion, a lithium ion, a phosphate ion, and the like in many cases. The first embodiment describes an example in which a sodium ion, a potassium ion, a chlorine ion are measured.

The cartridge 101 is filled with internal gel 107. The internal electrode 102 is fixed so that the internal electrode 102 is in contact with the internal gel 107. When the sample is introduced into the flow path 103, the ion-sensitive membrane 105 contacts the sample and generates electromotive force depending on the concentration of ions within the sample. Since the ion-sensitive membrane 105 is electrically conductive with the internal electrode 102 via the internal gel 107, a change in the electromotive force of the ion-sensitive membrane 105 can be measured by measuring a potential output by the internal electrode 102. Therefore, the concentration of ions within the sample can be calculated.

The semiconductor memory 106 is arranged on a portion separated from the internal gel 107 within the cartridge 101. The communication line 104 is connected to the semiconductor memory 104 and extends from the semiconductor memory 106 to the outside of the cartridge 101.

Figure 4:
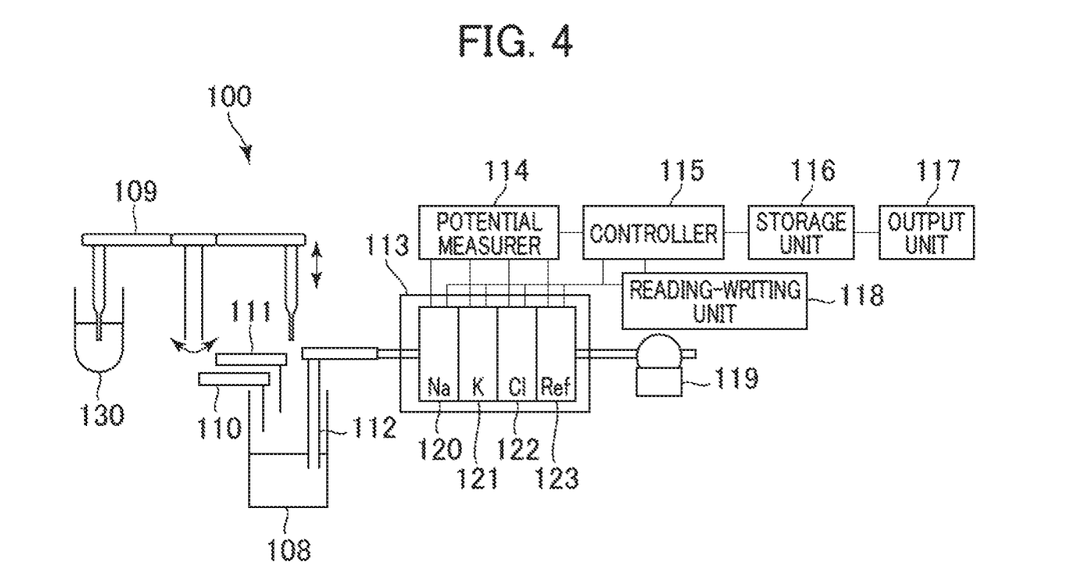
FIG. 4 is a schematic configuration diagram of the ion concentration measuring device 100.

FIG. 4 is a schematic configuration diagram of the ion concentration measuring device 100. A dilution tank 108 is provided to dilute the sample. A sample cup 130 holds the sample. A sample dispensing mechanism 109 dispenses the sample into the dilution tank 108. A dilution solution nozzle 110 discharges a dilution solution into the dilution tank 108. An internal reference solution nozzle 111 discharges an internal reference solution into the dilution tank 108. A sipper nozzle 112 sends the diluted sample and the internal reference solution from the dilution tank 108 to the flow path 103. An electrode installation unit 113 includes one or more cartridges that are the same as or similar to the cartridge 101. As described above, an example in which a Na detection cartridge 120, a K detection cartridge 121, and a Cl detection cartridge 122 are provided is described. A reference potential cartridge 123 also has the same configuration and outputs a reference potential to be used to measure a potential difference. A potential measurer 114 measures differences between potentials output by the internal electrodes 102 of the cartridges and a reference potential output by the internal electrode 102 of the reference potential cartridge 123. A controller 115 controls units of the ion concentration measuring device 100 and uses results of measurement by the potential measurer 114 to calculate the concentration of ions within the sample. A storage unit 116 stores the results of the calculation. An output unit 117 outputs data stored in the storage unit 116. A reading-writing unit 118 writes data such as the calculation results received from the controller 115 to the semiconductor memories of the cartridges or reads data from the semiconductor memories 106.

To measure the concentration of ions within the sample, the internal electrodes 102 of the cartridges are connected to the potential measurer 114, and the communication lines 104 are connected to the reading-writing unit 118. The flow paths 103 are connected to the sipper nozzle 112. The sample aspirated from the sipper nozzle 112 is sent to the flow paths 103 of the cartridges. The cartridges are electrically conductive with each other via the sample. The potential measurer 114 measures potentials output by the internal electrodes 102 of the cartridges using the potential output by the reference potential cartridge 123 as a standard.

The controller 115 supplies power to the semiconductor memories 106 in a time period excluding a time when the controller 115 acquires, from the potential measurer 114, the potentials output by the internal electrodes 102 of the cartridges. It is, therefore, possible to suppress effects of electrical noise generated from the semiconductor memories 106 and heat generated from the semiconductor memories 106 on results of the measurement based on the ion-sensitive membranes 105. A specific operational procedure is described using FIG. 5 described below.

Figure 5:
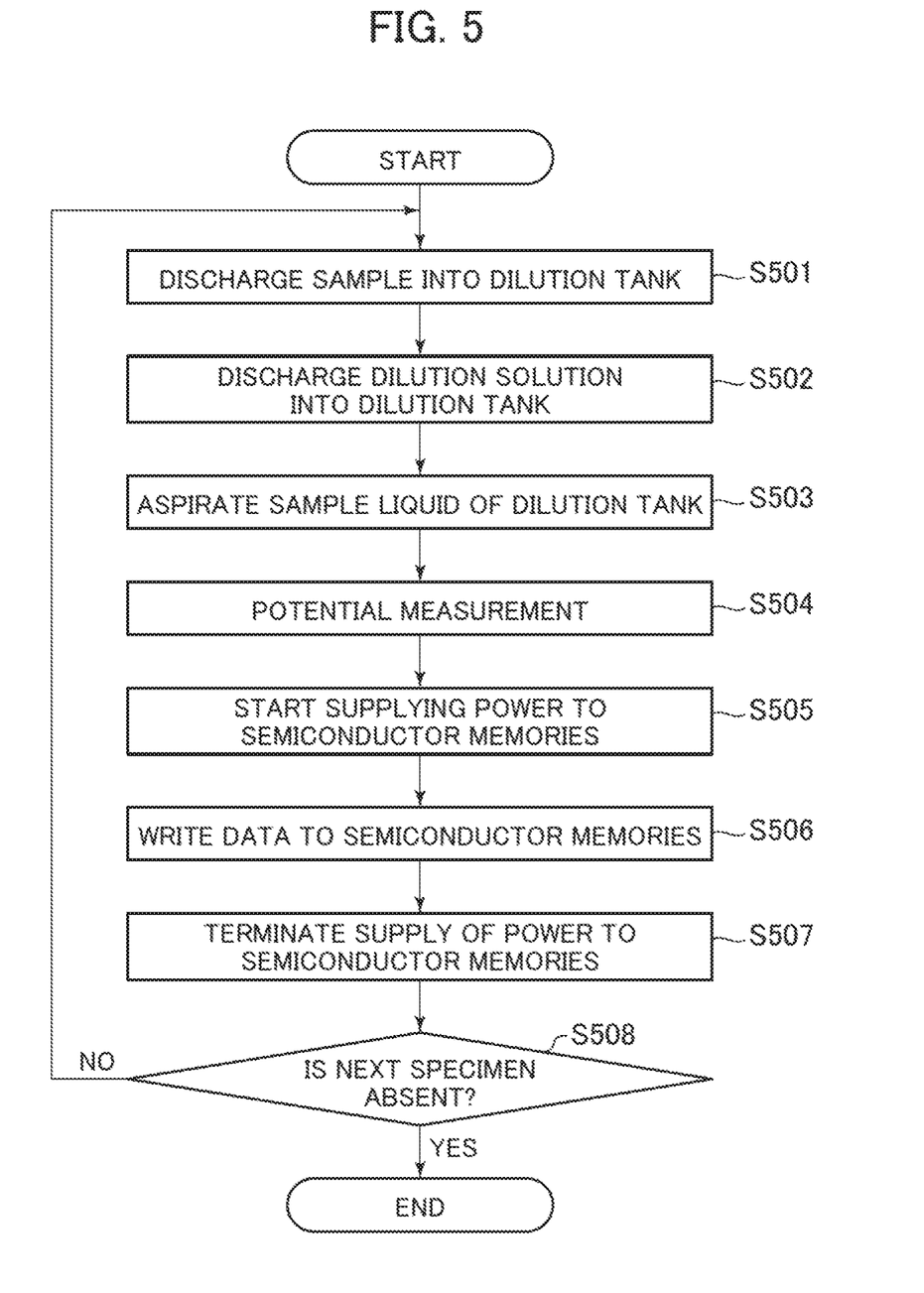
FIG. 5 is a flowchart describing a procedure for measuring the concentration of ions within a sample by the ion concentration measuring device 100.

FIG. 5 is a flowchart describing a procedure for measuring the concentration of ions within the sample by the ion concentration measuring device 100. Steps of FIG. 5 are described below.

(FIG. 5: Steps S501 and S502)

The sample dispensing mechanism 109 dispenses the sample within the sample cup 130 and discharges the sample into the dilution tank 108 (S501). The dilution solution nozzle 110 discharges the dilution solution into the dilution tank 108 to dilute the sample with the dilution solution (S502).

(FIG. 5: Step S503)

The sipper nozzle 112 aspirates the sample solution within the dilution tank 108 and sends the sample to the flow paths 103. Therefore, the flow paths 103 of the cartridges are filled with the sample, and an electric circuit that connects the cartridges to the potential measurer 114 via the sample solution is formed.

(FIG. 5: Step S504)

The potential measurer 114 uses the potential output by the reference potential cartridge 123 as a standard and measures potentials output by the internal electrodes 102 of the Na detection cartridge 120, the K detection cartridge 121, and the Cl detection cartridge 122. The controller 115 acquires the measurement results from the potential measurer 114 and uses the measurement results to calculate the concentration of ions within the sample. The controller 115 causes the calculation results to be stored in the storage unit 116.

(FIG. 5: Steps S505 to S507)

The controller 115 turns on power sources of the semiconductor memories 106 within the cartridges (or starts supplying power) (S505). The reading-writing unit 118 acquires the results of calculating the concentration of ions from the storage unit 116 and writes the results to the semiconductor memories of the cartridges (S506). The controller 115 turns off the power sources of the semiconductor memories 106 of the cartridges (or terminates the supply of power) (S507).

(FIG. 5: Step S508)

When a next specimen is waiting to be measured, the procedure returns to step S501 to measure the configuration of ions in the same procedure. When a specimen that is waiting to be measured does not exist, the flowchart is terminated.

First Embodiment: Conclusion

The ion concentration measuring device 100 according to the first embodiment turns on the power sources of the semiconductor memories 106 in a time period excluding a time when the controller 115 acquires changes in the potentials generated by the ion-sensitive membranes 105. It is, therefore, possible to suppress effects of electric noise generated from the semiconductor memories 106 and heat generated from the semiconductor memories 106 on results of measuring the potentials. This can improve the accuracy of the measurement while an advantage of each of the ion-selective electrodes is used.

The service life of the ion-sensitive membranes 105 is limited. Thus, after the ion-sensitive membranes 105 are used a certain number of times, the ion-sensitive membranes 105 need to be replaced. Since the cartridges 101 are attachable to and detachable from the ion concentration measuring device 100, the entire cartridges 101 can be replaced and thus are convenient. In addition, when the cartridges 101 are replaced, the semiconductor memories 106 included in the cartridges 101 can be recovered. A configuration in which the semiconductor memories 106 are installed in the cartridges 101 is useful from that point of view. On the other hand, conventionally, since an ion-sensitive membrane 105 is arranged in the vicinity of a semiconductor memory 106, an effect of electric noise or the like on a measurement result has been large. According to the first embodiment, it is possible to improve the accuracy of the measurement, while using the advantage that the semiconductor memories 106 are installed in the cartridges 101.

Second Embodiment

Figure 6:
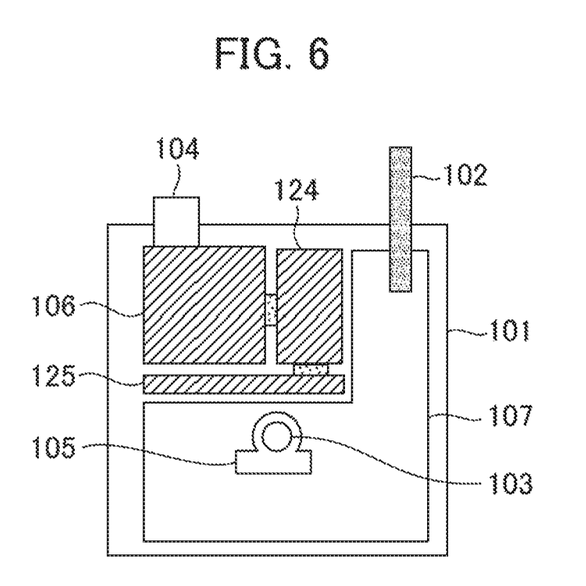
FIG. 6 is a cross-sectional view of a cartridge 101 included in an ion concentration measuring device 100 according to a second embodiment.

FIG. 6 is a cross-sectional view of a cartridge 101 included in an ion concentration measuring device 100 according to a second embodiment. In the second embodiment, each of the cartridges 101 includes a temperature sensor 125 and a temperature control device 124, as well as the configurations described in the first embodiment. Since other configurations are the same as or similar to those described in the first embodiment, different features related to these devices are mainly described below.

The temperature sensor 125 is a sensor for measuring the temperature of the ion-sensitive membrane 105. It is desirable that the temperature sensor 125 measure the temperature, for example, with accuracy of ±0.1° C. in a range of 0° C. to 50° C. The temperature sensor 125 does not necessarily need to be in contact with the ion-sensitive membrane 105. It is, however, desirable that the temperature sensor 125 be located in the vicinity of the ion-sensitive membrane 105 so that the temperature sensor 125 can measure at least a peripheral temperature around the ion-sensitive membrane 105.

The temperature control device 124 is a device that cools the ion-sensitive membrane 105 heated with heat generated from the semiconductor memory 106 to a temperature at which the concentration of ions can be accurately measured. Since it is sufficient if the temperature control device 124 cools at least a peripheral region that is in thermal contact with the ion-sensitive membrane 105, the temperature control device 124 does not necessarily need to be in direct contact with the ion-sensitive membrane 105. For example, the temperature control device 124 can be configured so that a flow path for a cooling medium is installed in the temperature control device 124 in the cartridge 101 and the cooling medium (for example, water, oil, or the like) is supplied from the outside of the cartridge 101. Furthermore, since the ion-sensitive membrane 105 is heated to an appropriate temperature, a thermoelectric element such as a Peltier element can be used. A cooling device and a heating device may be used.

The controller 115 receives measurement results from the temperature sensors 125 via the communication lines 104 and turns on and off the supply of power to the temperature sensors 125 and the temperature control devices 124. Since electric and thermal noise is generated due to operations of the temperature sensors 125 and the temperature control devices 124 in a similar manner to the semiconductor memories 106, the controller 115 supplies power to the temperatures 125 and the temperature control devices 124 in a time period excluding a time when the controller 115 receives the results of the measurement based on the ion-sensitive membranes 105.

Figure 7:
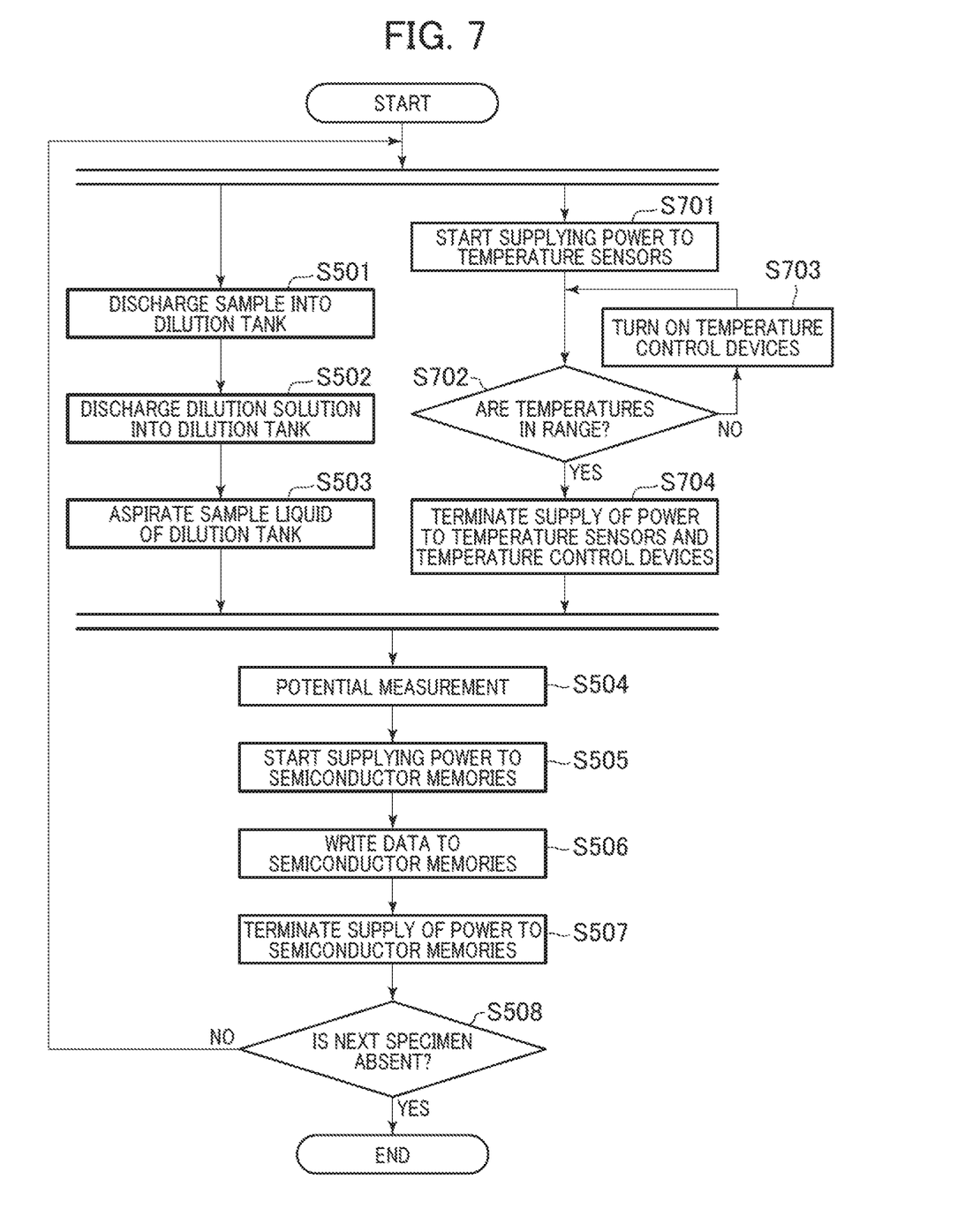
FIG. 7 is a flowchart describing a procedure for measuring the concentration of ions within the sample by the ion concentration measuring device 100 in the second embodiment.

FIG. 7 is a flowchart describing a procedure for measuring the concentration of ions within the sample by the ion concentration measuring device 100 according to the second embodiment. The ion concentration measuring device 100 performs steps S701 to S704 in parallel with steps S501 to S503 described with reference to FIG. 5. Since other steps are the same as or similar to FIG. 5, steps S701 to S704 are described below.

(FIG. 7: Step S701)

The controller 115 starts supplying power to the temperature sensors 125.

(FIG. 7: Step S702)

The temperature sensors 125 start measuring peripheral temperatures around the ion-sensitive membranes 105. The controller 115 acquires the measurement results. When the measured temperatures are in a predetermined range (or a range in which the ion-sensitive membranes 105 can output accurate measurement results), the procedure proceeds to step S704. Otherwise, the procedure proceeds to step S703. The temperature range in this step is determined based on necessary measurement accuracy. For example, it is desirable that the range is a range of ±1° C. of a reference measurement temperature.

(FIG. 7: Step S703)

The controller 115 supplies power to the temperature control devices 124 to cause the temperature control devices 124 to operate and adjust the peripheral temperatures around the ion-sensitive membranes 105 to a range (same range as that in step S702) suitable for the measurement. After this step, the procedure returns to step S702 to repeat the same processes.

(FIG. 7: Step S704)

The controller 115 stops supplying power to the temperature sensors 125 (and the temperature control devices 124 when step S703 has been performed).

Second Embodiment: Conclusion

The ion concentration measuring device 100 according to the second embodiment causes the temperature control devices 124 to adjust the peripheral temperatures around the ion-sensitive membranes 105 to a temperature suitable for the measurement. Therefore, for example, when amounts of heat generated from the semiconductor memories 106 are large and heat generated in the measurement of an initial specimen affects the measurement of a next specimen, or when heat generated from the semiconductor memories 106 is accumulated and the temperatures change during the time when a plurality of specimens are continuously measured, or the like, it is possible to reduce an effect on the measurement results.

Third Embodiment

The second embodiment describes the case where the temperature control devices 124 adjust the peripheral temperatures around the ion-sensitive membranes 105 in accordance with the measurement results of the temperature sensors 125. The measurement results of the temperature sensors 125 can be used for other purposes. A third embodiment describes a specific example thereof.

The ion-sensitive membrane 105 generally has a property varying depending on a temperature. For example, it is considered that characteristic data describing an association relationship between a potential generated by the ion-sensitive membrane 105 and the temperature of the ion-sensitive membrane 105 is stored in the storage unit 116 in advance and the controller 115 references the characteristic data and converts a potential output by the internal electrode 102 to the concentration of ions. For example, when a slope value changes depending on the temperature of the ion-sensitive membrane 105, the temperature property is stored as the characteristic data in advance, the concentration of ions can be calculated by referencing the characteristic data using the difference between the reference potential and the measured potential and the result of the measurement by the temperature sensor 125.

When the peripheral temperature around the ion-sensitive membrane 105 is high and is not suitable for the measurement, and the semiconductor memory 106 is further heated, the peripheral temperature further deviates from the temperature suitable for the measurement. Therefore, it is considered that, in the case where the measurement result of the temperature sensor 125 exceeds the temperature suitable for the measurement of the ion-sensitive membrane 105, as the temperature is higher, the rate of writing to the semiconductor memory 106 is reduced. This is due to the fact that, when the writing rate is reduced, it is possible to suppress the generation of heat from the semiconductor memory 106.

When the writing rate is reduced, there is a possibility that the writing is not completed in a time period up to the time when step S504 is performed next. In this case, remaining data that has not been completely written may be temporarily stored in the storage unit 116 and written again when step S506 is performed next.

Fourth Embodiment

The first to third embodiments describe the example in which, in a time period excluding a time when the controller 115 acquires changes in the potentials generated by the ion-sensitive membranes 105, the controller 115 turns on the power sources of the semiconductor memories 106, and when the controller 115 acquires the changes in the potentials generated by the ion-sensitive membranes 105, the controller 115 turns off the power sources of the semiconductor memories 106. When noise levels of the potentials can be suppressed to a level equal to or lower than a level that may cause a problem, the controller 115 does not necessarily need to turn off the power sources of the semiconductor memories 106 when the controller 115 acquires the changes in the potentials. For example, each of the semiconductor memories 106 and the controller 115 can have a normal mode and a standby mode.

The normal mode is a mode in which power to be supplied to the semiconductor memories 106 is normal. Specifically, rated values are used as a supply voltage and an operation frequency, and high throughput can be obtained by using the functions of the semiconductor memories 106 and the functions of the controller 115 without a restriction. The standby mode is a mode in which power to be supplied to the semiconductor memories 106 is suppressed. Specifically, it is possible to suppress power consumption and reduce the occurrence of noise by any or a combination of methods that are a reduction in the supply voltage, a reduction in the operation frequency, the stop of an operation of a circuit block having a function other than a minimally necessary function (for example, a function necessary for hot start described later), and the like. The standby mode is referred to as sleep mode, power saving mode, idling mode, low-speed mode, low-voltage mode, temporal stop mode, or the like in some cases.

In the case where the mode is returned from the standby mode to the normal mode (this is referred to as hot start, warm start, or the like), the normal mode can be quickly activated, compared to the case where the normal mode is activated from a state in which the power sources are completely turned off (this is referred to as cold start or the like). This is due to the fact that, in the standby mode, a part of an initialization process or the entire initialization process can be omitted by holding at least a part of (or all of) information realizing a state in which the normal mode is activated in a static memory, a register, or the like. There is an effect of suppressing electric noise and heat generated from the semiconductor memories 106, the communication lines 104, and the reading-writing unit 118 and suppressing an effect on results of measuring the potentials by appropriately selecting the supply voltage, the operation frequency, a range of circuit blocks to function, and the like in the standby mode and using the standby mode when the controller 115 acquires the changes in the potentials.

Compared to the case where the power sources of the semiconductor memories 106 are completely turned off when the controller 115 acquires the changes in the potentials, there are effects in which the activation is quickly completed and a time efficiency is high, since the standby mode is used and the high-speed hot start process (instead of the cold start that takes time) is used for the reading-writing unit 118 to perform the writing (S506) of results of calculating the concentration of ions to the semiconductor memories. Of course, when the standby mode is used concurrently, there is an effect in which power consumption is low, compared to the case where the operation is performed in the normal mode through all the processes.

Combining the method, described in the first to third embodiments, of turning off the power sources of the semiconductor memories 106 when the controller 115 acquires the changes in the potentials with the standby mode described in the fourth embodiment can be regarded as the standby mode in a broad sense. In this case, the method of turning off the power sources can be considered as an extreme example of one of standby modes in a broad sense. This is due to the fact that turning off the power sources maximally suppresses power to be supplied to the semiconductor memories 106 and, in other words, reduces power to be supplied to zero.

Regarding Modification Examples of the Invention

The invention is not limited to the foregoing embodiments and includes various modification examples. For example, the foregoing embodiments are described in detail to clearly explain the invention and are not necessarily limited to all the configurations described. In addition, some of configurations described in a certain embodiment can be replaced with configurations described in another embodiment. Furthermore, a configuration described in a certain embodiment can be added to a configuration described in another embodiment. Furthermore, a configuration can be added to, removed from, or replaced with a part of the configurations of each of the embodiments.

The foregoing embodiments describe the example in which the ion-sensitive membranes 105 are electrically connected to the internal electrodes 102 via the internal gel 107. Instead of this, a technique that does not use the internal gel 107 and is referred to as solid electrode may be used. In this case, instead of the internal gel 107, a carbon fiber, metal such as silver, platinum, gold, or iron, or a conductive material such as an ion liquid is used to electrically conduct the ion-sensitive membranes 105 and the internal electrodes 102.

The foregoing embodiments describe the example in which power is supplied to the semiconductor memories 106 and data is written every time a specimen is measured. These operations may be performed in another time period excluding a time when step S504 is performed. For example, when the ion concentration measuring device 100 is activated or terminated, data held in the storage unit 116 may be collectively written.

The second embodiment describes the example in which the temperature sensor 125 and the temperature control device 124 are installed in each of the cartridges 101. This is due to the fact that it is desirable that these devices be arranged in the vicinity of the ion-sensitive membrane 105 to control the temperature. As long as equivalent functions can be realized, the temperature sensor 125 and the temperature control device 124 may be arranged outside each of the cartridges 101 as constituent elements of the ion concentration measuring device 100.

As the data to be written to the semiconductor memories 106, not only the results of calculating the concentration of ions but also data useful for analysis after the cartridges 101 are recovered can be written. For example, the following items can be considered: (a) a time and date when the controller 115 calculates the concentration of ions or a time and date when the results of the calculation are written; (b) identifiers (manufacturing IDs or the like) of the ion-sensitive membranes 105 or the cartridges 101; (c) a manufacturing date of the ion-sensitive membranes 105 or the cartridges 101; (d) an expiration date of the ion-sensitive membranes 105 or the cartridges 101; (e) the results of calculating the concentration of ions by the controller 115 in a process of calibrating the cartridges 101; and (f) an alarm history (including an alarm occurrence time and date and the like) indicating that ion concentration calculated by the controller 115 is not in a reference range.

The controller 115 and the reading-writing unit 118 can be configured using hardware such as a circuit device having the functions of these units or can be configured by causing an arithmetic device to execute software having the functions of these units. The storage unit 116 can be constituted by, for example, a storage device such as a hard disk device.

LIST OF REFERENCE SIGNS

100: Ion concentration measuring device
101: Cartridge
102: Internal electrode
103: Flow path
104: Communication line
105: Ion-sensitive membrane
106: Semiconductor memory
107: Internal gel
108: Dilution tank
109: Sample dispersing mechanism
110: Dilution solution nozzle
111: Internal reference solution nozzle
112: Sipper nozzle
113: Electrode installation unit
114: Potential measurer
115: Controller
116: Storage unit
117: Output unit
118: Reading-writing unit
119: Pump
120: Na detection cartridge
121: K detection cartridge
122: Cl detection cartridge
123: Reference potential cartridge
124: Temperature control device
125: Temperature sensor

The invention claimed is:

1. An ion concentration measuring device that measures the concentration of ions contained in a solution, comprising:
   an ion detection element that generates a first potential based on the concentration;
   a first electrode that outputs the first potential;
   a memory that stores data;
   a reader-writer that writes data to the memory or reads data from the memory; and
   a controller that uses the first potential to calculate the concentration, wherein
   the ion detection element and the memory are installed in a first cartridge,
   the memory has a normal mode in which normal power is supplied and a standby mode in which the supply of power is suppressed,
   the controller sets the memory to the normal mode in a memory access period excluding a potential measurement period for which the controller acquires a potential value corresponding to the first potential output by the first electrode, and
   the controller sets the memory to the standby mode when the memory access period is complete,
   the ion concentration measuring device further comprising:
   a temperature sensor that measures a peripheral temperature around the ion detection element; and
   a temperature control device that adjusts the peripheral temperature around the ion detection element in accordance with the result of the detection by the temperature sensor, wherein
   the controller is configured to reduce a rate of writing to the memory in response to the peripheral temperature around the ion detection element detected by the temperature sensor exceeding a temperature suitable for measurement by the ion detection element to suppress the amount of heat generated from the memory in the writing of the data to the memory.

2. The ion concentration measuring device according to claim 1, wherein
the controller blocks the supply of power to the memory in the standby mode.

3. The ion concentration measuring device according to claim 1, wherein
the controller supplies power to the temperature sensor and the temperature control device in a temperature control period excluding the potential measurement period, and
the controller blocks the supply of power to the temperature sensor and the temperature control device when the temperature control period is complete.

4. The ion concentration measuring device according to claim 1, wherein
the reader-writer writes, to the memory, at least any of a result of calculating the concentration, a time and date when the concentration has been calculated, an identifier of the ion detection element, a manufacturing date of the ion detection element, an expiration date of the ion detection element, a result of calculating the concentration in a process of calibrating the ion detection element, and an alarm history indicating that the result of calculating the concentration is not in a reference range.

5. The ion concentration measuring device according to claim 1, further comprising:
a storage unit that stores characteristic data describing an association relationship between a potential generated by the ion detection element and a temperature of the ion detection element, wherein
the controller calculates the concentration by referencing the characteristic data using the result of the detection by the temperature sensor.

6. The ion concentration measuring device according to claim 1, wherein
when data is not completely written to the memory in the memory access period, the controller temporarily holds the data that has not been written, and when the memory access period has come next, the controller writes, to the memory, the data that has not been written.

7. The ion concentration measuring device according to claim 1, wherein
the temperature sensor and the temperature control device are installed in the first cartridge.

8. The ion concentration measuring device according to claim 1, wherein
the first cartridge further includes gel that is in electrical contact with the ion detection element and the first electrode, and
the first cartridge has a through-hole that causes the solution to flow to make fluid contact with the ion detection element.

9. The ion concentration measuring device according to claim 1, wherein
the first cartridge is configured so that the first cartridge is attachable and detachable to and from the ion concentration measuring device.

10. The ion concentration measuring device according to claim 1, further comprising:
a second cartridge including a second electrode that outputs a second potential; and
a potential measurer that measures a potential difference between the first potential and the second potential, wherein
the controller uses the potential difference to calculate the concentration.

11. The ion concentration measuring device according to claim 1, further comprising:
a Na ion detection cartridge including a Na ion detection element that generates a potential based on the concentration of Na ions;
a K ion detection cartridge including a K ion detection element that generates a potential based on the concentration of K ions; and
a Cl ion detection cartridge including a Cl ion detection element that generates a potential based on the concentration of Cl ions.

* * * * *